(12) United States Patent
Sandstrom

(10) Patent No.: US 9,757,582 B2
(45) Date of Patent: Sep. 12, 2017

(54) TUMOR TREATMENT WITH FREE RADICAL LIFETIMES ENHANCED BY PERSISTANT LOW STRENGTH MAGNETIC FIELD

(71) Applicant: Robert E. Sandstrom, Longview, WA (US)

(72) Inventor: Robert E. Sandstrom, Longview, WA (US)

(*) Notice: Subject to any disclaimer, the term of this patent is extended or adjusted under 35 U.S.C. 154(b) by 219 days.

(21) Appl. No.: 14/356,747

(22) PCT Filed: Oct. 25, 2013

(86) PCT No.: PCT/US2013/066820
§ 371 (c)(1),
(2) Date: May 7, 2014

(87) PCT Pub. No.: WO2014/066765
PCT Pub. Date: May 1, 2014

(65) Prior Publication Data
US 2014/0316185 A1 Oct. 23, 2014

Related U.S. Application Data

(60) Provisional application No. 61/718,896, filed on Oct. 26, 2012.

(51) Int. Cl.
*A61N 2/00* (2006.01)
*A61N 5/10* (2006.01)
*A61N 2/06* (2006.01)
*A61N 7/00* (2006.01)
*A61N 2/02* (2006.01)

(52) U.S. Cl.
CPC ............... *A61N 2/002* (2013.01); *A61N 5/10* (2013.01); *A61N 5/1031* (2013.01); *A61N 2/02* (2013.01); *A61N 2/06* (2013.01); *A61N 7/00* (2013.01)

(58) Field of Classification Search
CPC .......... A61N 2/00; A61N 2/002; A61N 2/004; A61N 2/006; A61N 2/008; A61N 2/02;
(Continued)

(56) References Cited

U.S. PATENT DOCUMENTS 5,358,503 A * 10/1994 Bertwell et al. ................. 606/27
6,099,459 A * 8/2000 Jacobson ......................... 600/13
(Continued)

FOREIGN PATENT DOCUMENTS

RU 2195981 C2 1/2003

OTHER PUBLICATIONS

Long-Lived Mutagenic Radicals Induced in Mammalian Cells by Ionizing Radiation are Mainly Localized to Proteins, Iun Kumagai, Kiyonao Masui, Yoshiteru Itagaki, Masaru Shiotani, Seiji Kodama, Masami Watanabe, and Tetsuo Miyazaki, Radiation Research, 160(1):95-102.2003, Radiation Research Society, http://dx.doi.orgll0.1667/RR3015,http://www.bioone.orgidoi/full/10.16671RR3015.
(Continued)

*Primary Examiner* — Charles A Marmor, II
*Assistant Examiner* — Carrie R Dorna
(74) *Attorney, Agent, or Firm* — Timothy E. Siegel Patent Law, PLLC; Timothy E. Siegel

(57) ABSTRACT

In the treatment of a tumor (126) with radiation therapy (122) is enhanced by a weak magnetic field (130), the field strength time sequence of exposure and shape and contour of the magnetic field are varied to achieve desired results. In one separate aspect, exposure to a magnetic field (130) is continued after exposure to a free radical-creating therapy is ceased or diminished, thereby increasing the lifetimes of free radicals that have already been created. In another preferred embodiment a magnetic field (13) is strategically placed to avoid extending the lives of free radicals in tissue through
(Continued)

which a free radical-creating beam must pass, to reach a tumor. This application discloses quantitative parameters for field strength and exposure time to create concentrations and reactivity of free radicals, including long-lived free radicals and discloses the use of shaped, contoured, and designed electromagnetic fields. A treatment planning station (200) is also disclosed.

23 Claims, 6 Drawing Sheets

(58) Field of Classification Search
CPC ... A61N 2/06; A61N 2/12; A61N 5/10; A61N 5/1001; A61N 5/1007; A61N 5/1014; A61N 5/1027; A61N 5/1028; A61N 5/1069; A61N 5/107; A61B 2034/2055
USPC .............. 600/9–15; 607/1, 3, 59, 61, 66, 67, 607/72–76
See application file for complete search history.

(56) References Cited

U.S. PATENT DOCUMENTS

| | | | |
|---|---|---|---|
| 6,443,978 B1* | 9/2002 | Zharov | 607/91 |
| 6,507,751 B2* | 1/2003 | Blume et al. | 600/424 |
| 6,926,659 B1 | 8/2005 | Sandstrom | |
| 7,333,852 B2* | 2/2008 | Palti | 607/2 |
| 8,684,901 B1* | 4/2014 | Zabara | 600/14 |
| 2005/0187424 A1* | 8/2005 | Hambuchen | A61B 34/70 600/12 |
| 2006/0079942 A1* | 4/2006 | Deno et al. | 607/17 |
| 2006/0231110 A1* | 10/2006 | Mintchev | A61B 5/053 128/899 |
| 2006/0285639 A1* | 12/2006 | Olivera | A61N 5/1042 378/65 |
| 2009/0005631 A1* | 1/2009 | Simenhaus et al. | 600/9 |
| 2011/0004450 A1* | 1/2011 | Mishelevich et al. | 703/2 |
| 2012/0226093 A1 | 9/2012 | Creighton | |

OTHER PUBLICATIONS

Radiation-induced long-lived radicals which cause mutation and transformation, Shinji Koyama, Seiji Kodama, Keiji Suzuki, Takurou Matsumoto,Tetsuro Miyazaki, Masami Watanabe, Laboratory of Radiation and Life Science, School of Pharmauutkal Sciences, Nagasaki University, Nagasaki, Japan, Jan. 6, 1998.

Free Radical Initiation in Proteins and Amino Acids by Ionizing and Ultraviolet Radiations and Lipid Oxidation, K. M. Schaich, Medical Department, Brookhaven National Laboratory, Upton, Long Island, New York, Oct. 1980.

* cited by examiner

TUMOR TREATMENT WITH FREE RADICAL LIFETIMES ENHANCED BY PERSISTANT LOW STRENGTH MAGNETIC FIELD

TECHNICAL FIELD

The present invention relates to methods and devices for treating malignant tumors. More specifically the present invention relates to methods and devices for killing tumor cells by creating free radicals in a tumor, and extending the lifetime and modifying the reaction kinetics of the free radicals by exposing them to a magnetic field.

BACKGROUND ART

A central problem in cancer treatment is that of preserving healthy tissue while destroying cancerous tissue. Although radiation therapy generally involves the focusing of radiation on a tumor, at least some healthy tissue generally is located in the irradiated field. This healthy tissue is exposed to and to some degree damaged by the radiation. In chemotherapy healthy tissue is exposed to the chemotherapy agent and may be damaged.

Moreover, research has shown that much of the effect of radiation therapy and a substantial component of some approaches to chemotherapy are mediated by free radical effects in tumor tissue. The mechanisms whereby free radicals produce tumor cell death include direct enzymatic effects, DNA damage and induction of apoptotic pathways.

Our understanding of the physics and chemistry of free radicals and paired radicals has gradually increased over the past ten years. A free radical is any chemical species capable of an independent existence that has an unpaired electron in its valence shell. The presence of an unpaired electron in the valence shell causes free radicals to be paramagnetic and exhibit magnetic properties when exposed to a magnetic field.

Free radicals may be formed by any of several mechanisms including but not limited to: Ultraviolet induced homolytic fission as may be encountered in laser ablation therapy of tumors; Specific chemical reactions as encountered with pharmacological chemotherapy e.g. bleomycin; Ionizing radiation as the result of external beam irradiation, antibody directed or site selective radio-nucleotide administration or through implantation radiotherapy e.g. prostatic brachyotherapy; Thermal induction as in hyperthermic therapy; or Ultrasound induced acoustic cavitation.

Free radicals once generated may recombine. The biologic effects of free radicals in tissue are determined by the net reactive fraction namely the "escape" population that does not recombine rapidly. Factors, which influence pair recombination, include the viscosity of the reaction environment, temperature, bystander effects and the quantum state of the free radical. The quantum state of the free radical is defined by the applicable Schrodinger equation (H.PSI.=E.PSI.) where H is a Hamiltonian operator and .PSI. are sets of wave functions (Eigenfunctions). The Eigenfunctions are defined by a set of four quantum numbers: n—the principal quantum number, 1—the orbital quantum number, $M_1$—the magnetic quantum number and $M_s$—the spin quantum number. Of particular significance to this discussion is the spin quantum number.

The spin quantum number for an unpaired orbital electron can assume one of two values either +½ or ½. The wave distribution function determined by spin quantitization is a vector quantity and subject to influence by a superimposed magnetic field. When two electrons share an orbital space they must have opposite spin polarity. This phenomenon is dictated by the Pauli Exclusion Principal that postulates that no two electrons can occupy the same quantum state.

Spin polarity is conventionally referred to as up spin (.uparw.) +½ or down spin (.dwnarw.)−½. Shared valence electrons in the formation of chemical bonds also must have opposite spin polarity. When covalent bonds are severed as in the formation of free radicals spin polarity is preserved.

The unpaired electron in the valence orbital of a free radical in a magnetic field will precess in a manner comparable to Larmor precession described for charged particles in classic electrodynamics. Quantum precession leads to spin phase transitions between the singlet state where antiparallel spin vectors apply and triplet states where parallel spin vectors apply. The singlet state is favorable for recombination because antiparallel spin orientation is preserved and a covalent bond can be established. Triplet state configurations are unfavorable for recombination because parallel spin orientation is induced. In a magnetic field there are three triplet state configurations, which are vector quantities that due to precession in the magnetic field are no longer energy equivalent and are said to be nondegenerate.

The strength of the applied magnetic field, which maximizes the spin phase mixing effect, is dependent on the quantum state of the free radical or the system of free radicals. In general optimum phase mixing is achieved at relatively low magnetic field strengths (0.1-10.0 mTesla) within the hyperfine coupling energy levels of the radical pair.

The singlet state ($S_1$) characterized by antiparallel spin vectors will prevail in the absence of a magnetic field when homolytic fission of a covalent bond occurs to form a free radical pair. In the presence of a magnetic field of appropriate strength, the triplet states, $T_{-1}$, $T_0$ and $T_{-1}$ are equally probable energy states and are distinct and nondegenerate. The theoretic distribution between singlet and triplet states will be 25% singlet and 75% triplet. Such a distribution will theoretically increase the effective concentration of escape radicals by 75%. In experimental situations the yield is limited by non-quantum factors including viscosity effects, temperature, diffusion and bystander effects. However, increases in escape radical reactivity of 20-40% are documented in experimental systems where free radical escape reactions are measured.

U.S. Pat. Nos. 6,679,827 and 6,926,659 disclose a method for enhancing irradiation tumor treatment by creating a magnetic field that intersects with the irradiating beam in the area of the tumor. Referring to FIG. 1, showing a technique disclosed in these patents, a patient's body 10 is subjected to radiation 12 that travels through the body 10 in a first direction. A magnet 18 is oriented so as to create a magnetic field 20 in the vicinity of a tumor 22 of one milli-Tesla (mT). In another technique disclosed, shown in FIG. 2, a tumor 22 may be treated by placing radioactive strips 30 about it. Additionally, magnetic strips 32 are placed to create a magnetic field in the tumor 22. Referring to FIG. 3, in another prior art technique, a laparoscope 40 is used to introduce a magnet 42 directly into the tumor. Finally, referring to FIG. 4, a tumor may be treated by a set of radioactive beads 50 and a set of magnetic beads 52, adapted to create a magnetic field. The treatment described is time static in the sense that the irradiating beam and the magnetic field are disclosed as being simultaneous.

Much of the clinical efficacy of radiation therapy tumor treatment stems from actions by ionization-induced free radical production and changes in their combinatorial kinetics. Although it has been shown that weak magnetic fields influence free radical behavior in irradiated tissue, this knowledge has not been fully exploited in the treatment of tumors.

DISCLOSURE OF THE INVENTION

In the treatment of a tumor with radiation therapy enhanced by a weak magnetic field, the field strength time sequence of exposure and the shape and contour of the magnetic field are varied to achieve desired results. In one separate aspect, exposure to a magnetic field is continued after exposure to a free radical-creating therapy is ceased or diminished, thereby increasing the lifetimes of free radicals that have already been created. In another preferred embodiment a magnetic field is strategically placed to avoid extending the lives of free radicals in tissue through which a free radical-creating beam must pass, to reach a tumor. This application discloses quantitative parameters for field strength and exposure time to create concentrations and reactivity of free radicals, including long-lived free radicals and discloses the use of shaped, contoured, and designed electromagnetic fields. A treatment modeling station is also disclosed.

BEST MODES OF CARRYING OUT THE INVENTION

In a preferred set of embodiments, free radicals created to kill tumor cells have their lifetimes extended by a weak magnetic field (in the range of 10 to 100 gauss), shaped and timed to extend free radical lifetimes in the tumor, while avoiding to the extent possible, extending free radical lifetimes in surrounding tissue.

In one preferred embodiment tumor cells are exposed to levels of 2 to 6 Gy of Co-60 gamma radiation (IR) stimulus, with simultaneous exposure to DC field strengths ranging from 10 to 100 gauss (0.5 to 10 millitesla), with the DC electromagnetic field exposure continuing for up to one hour after cessation of the IR. In other preferred embodiments other forms of stimulus for producing free radicals are used, including chemotherapy, other forms of radiation and exposure to induced ultrasound, ultraviolet, thermal, or sonic cavitation energy. Magnetic field persistence after cessation of stimulus is between 1 minute and 10 hours.

Figure 1:
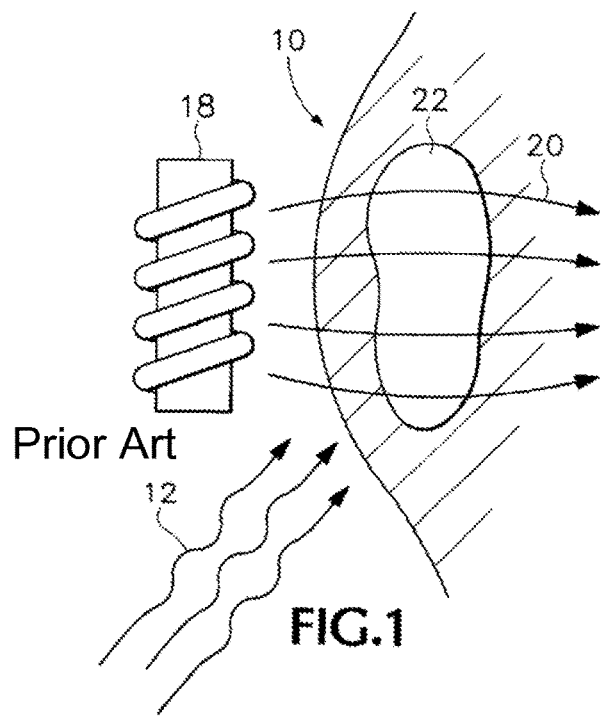
FIG. 1 is an illustration of a tumor being treated by radiation therapy augmented by a magnetic field.
Figure 2:
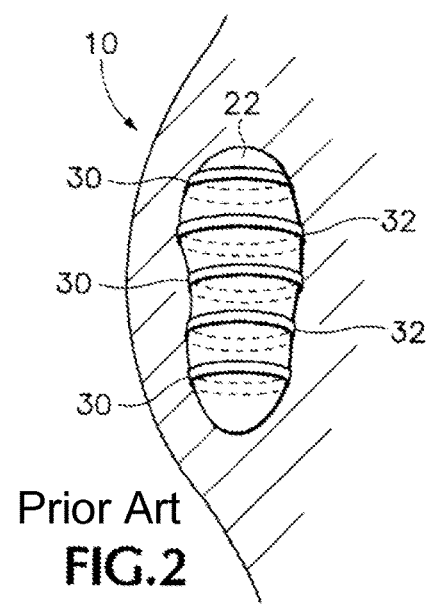
FIG. 2 is an illustration of a tumor being treated by strips of implanted radioactive material interspersed with strips of implanted magnetic material.
Figure 3:
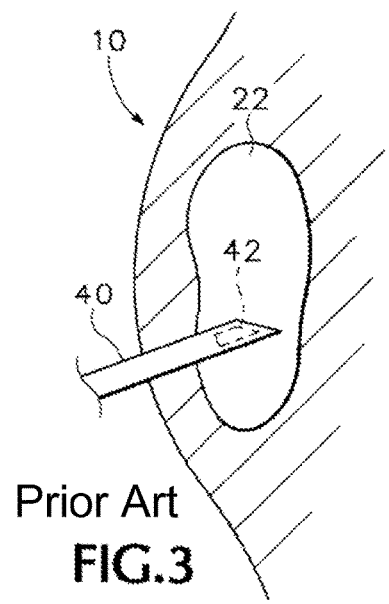
FIG. 3 is an illustration of a tumor into which a magnet has been introduced by a laparoscope.
Figure 4:
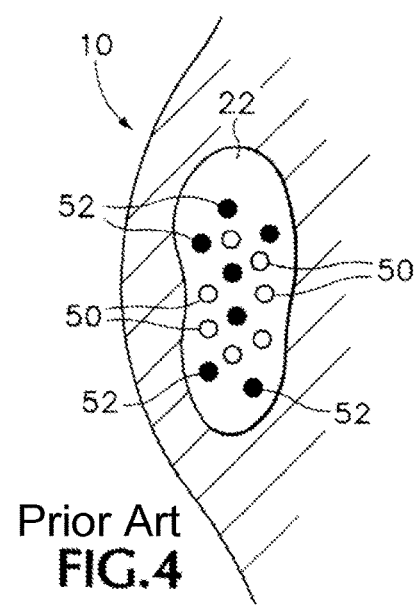
FIG. 4 is an illustration of a tumor that is being treated by a combination of radioactive beads and magnetic beads.
Figure 5:
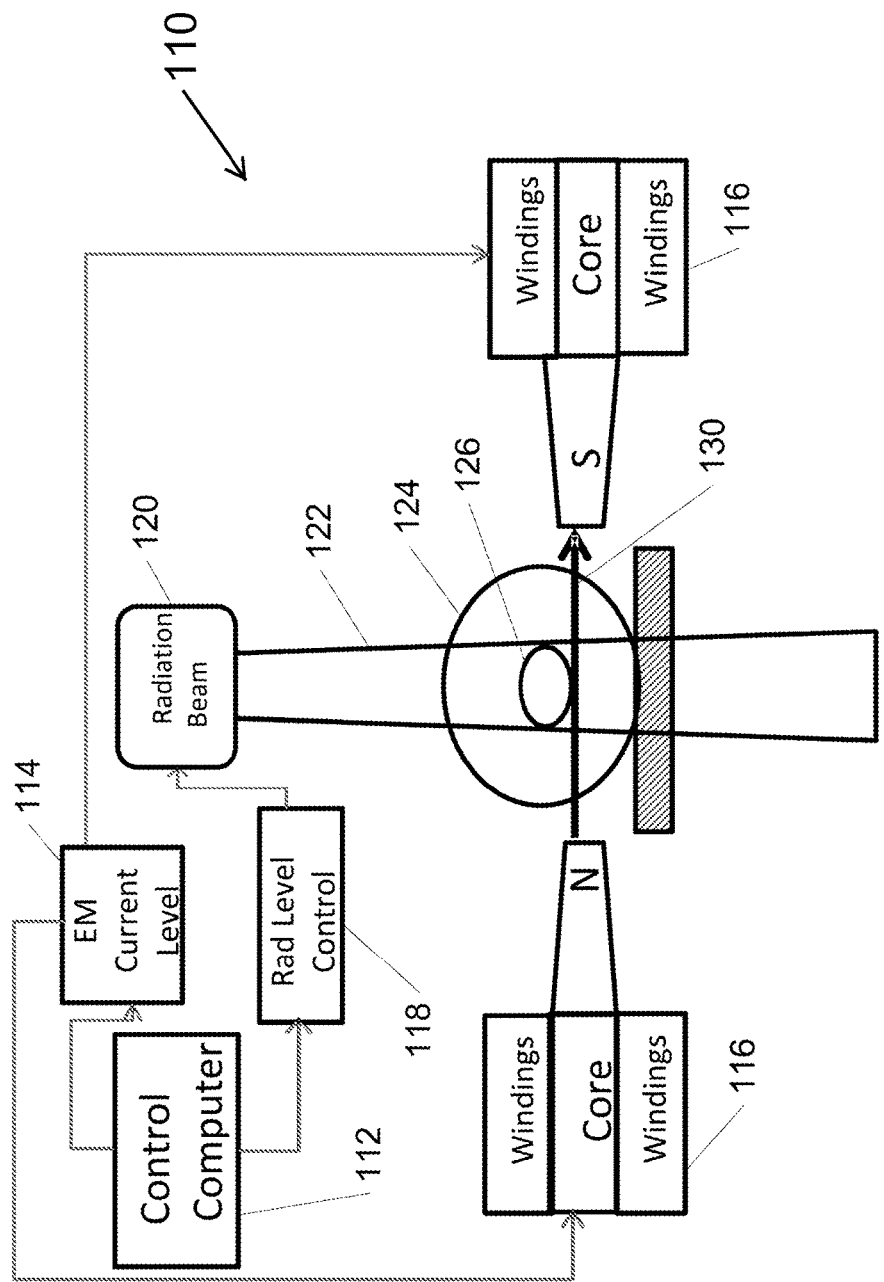
FIG. 5 is an illustration of a tumor that is being treated by a combination of irradiation and a magnetic field created by two electromagnets.
Figure 6:
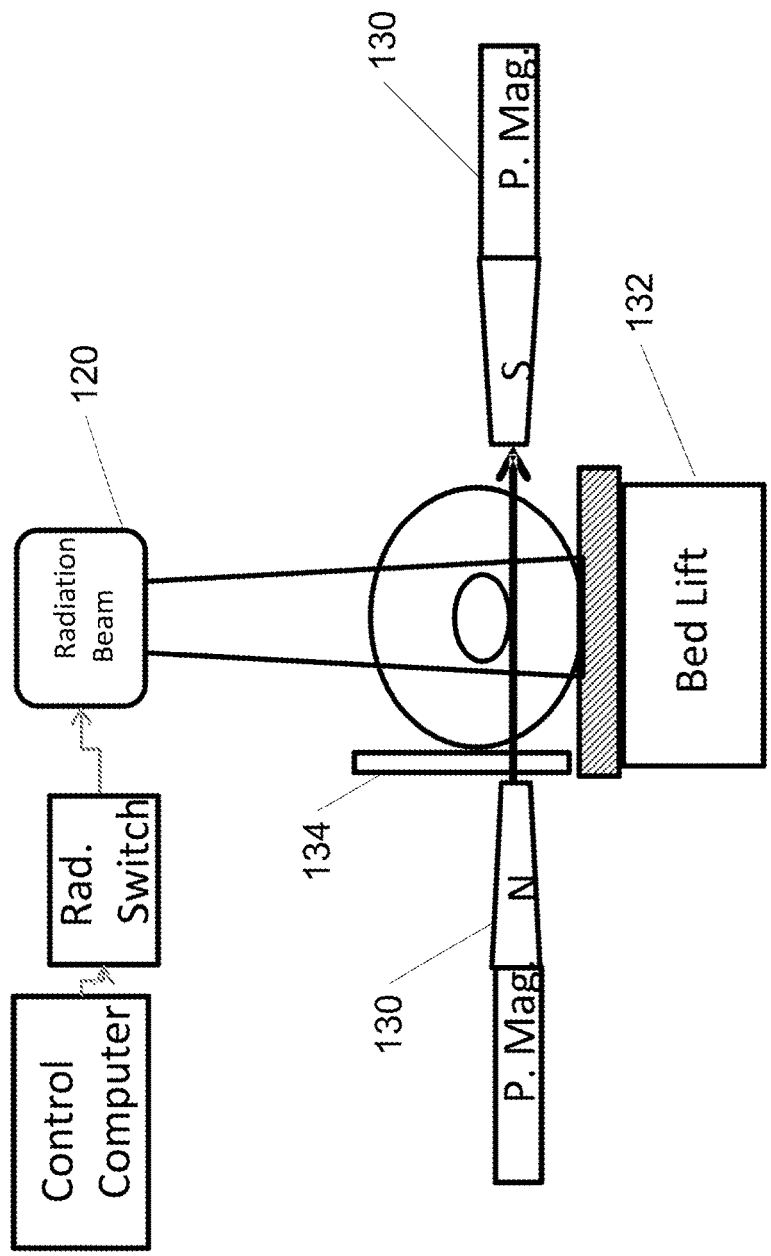
FIG. 6 is an illustration of a tumor that is being treated by a combination of irradiation and a magnetic field created by two permanent magnets.

Referring to FIG. 5, in one preferred embodiment, a machine 110 is used to provide the tumor treating radiation and magnetic field. A control computer 112, controls an electromagnetic current source 114, which controls the electromagnets 116, including turning them off and/or rapidly sequencing a planned variable strength field. The computer 112 also controls the radiation beam level control 118, which controls the intensity of the radiation beam 122, from the radiation beam source 120. Radiation beam 122 travels through a human body 124 and reaches and travels through a tumor 126. An electromagnetic field, having axis 130 helps to perpetuate free radicals produced by the radiation beam 122. FIG. 6 shows a machine that is the same as that of FIG. 5, except for that permanent magnets 130 are used, in order to produces a very thin magnetic field, to restrict the magnetic field effects as much as possible to the tumor. Because it is beneficial for magnets 130 to be very accurately aligned, in one embodiment they are not moved, but the patient is moved upwardly by a bed lift mechanism 132, so that magnets 130 can be laser aligned prior to a patient being treated, without having to be moved into position after alignment, which could cause some of the precision of the alignment to be lost during this movement. A magnetic field interrupting mechanism 134 (in one embodiment mounted on a rotating shaft) can be used to block the magnetic field, in one embodiment in a periodic manner coordinated with the radiation beam source 120 and contoured to conform to tumor shape. Skilled persons will recognize from FIGS. 5 and 6 that electromagnets 116 and permanent magnets 130 are aligned along their longitudinal axes. In a preferred embodiment, electromagnets 116 have a length at least 20 cm, and a thickness of less than 1 cm. Likewise, in a preferred embodiment, permanent magnets have a length at least 20 cm and a thickness of less than 1 cm. In both instances, in a preferred embodiment, magnets 116 or 130 are spaced no more than 50 cm apart.

Figure 7:
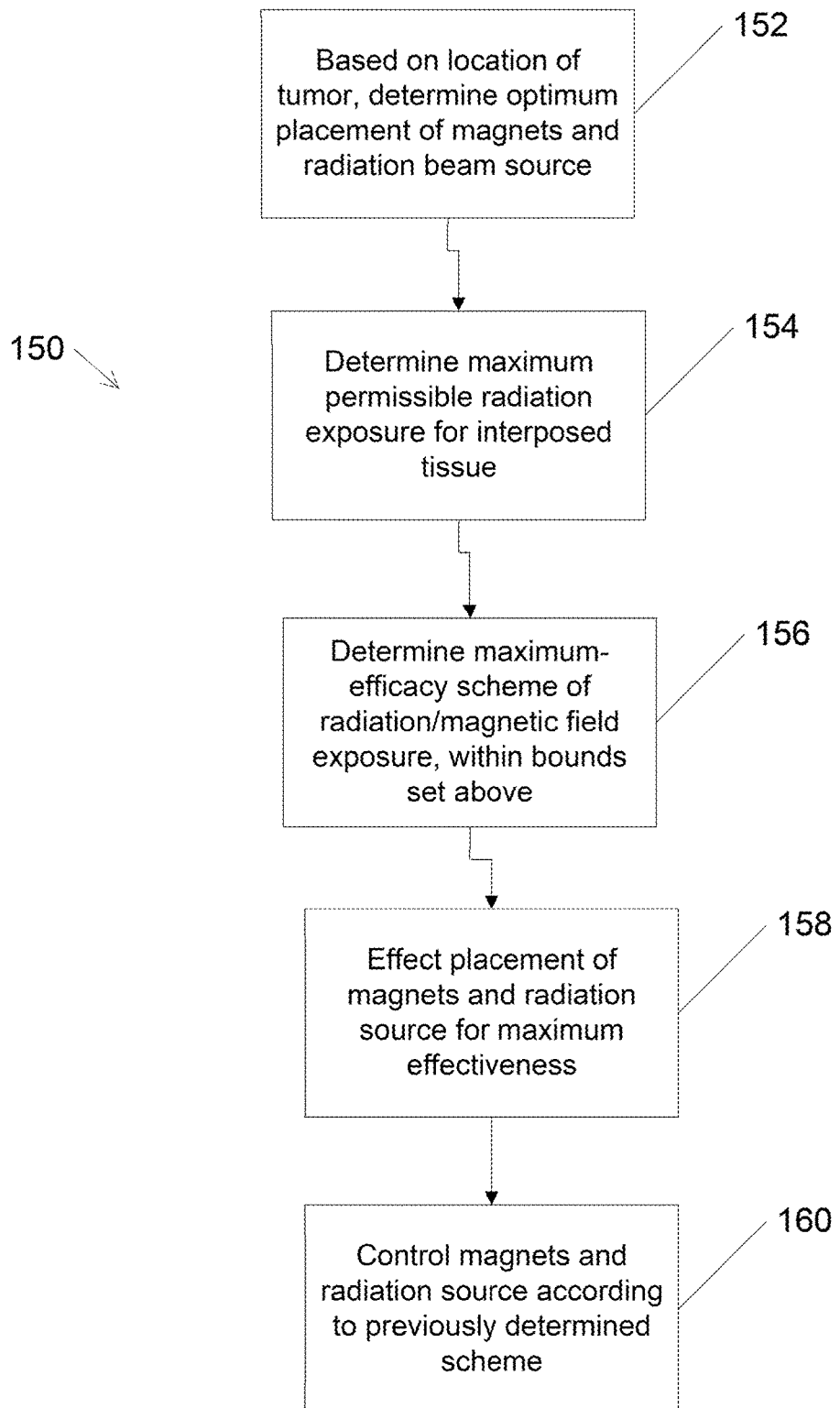
FIG. 7 is a flow chart of a method of treating a tumor.

Referring to FIG. 7, showing a preparation and treatment scheme 150 begins with a determination, based on tumor location, of the positioning of magnets 116 (FIG. 5) and radiation beam source 120 (block 152). Then, given these locations, the maximum permissible radiation exposure for the interposed tissue is computed (block 154). Next, given these limits, the maximum effectiveness scheme of exposure to a radiation beam and a magnetic field is determined (block 156). As it is impossible to expose only the tumor to the magnetic field, the effect of the magnetic field on the radiation beam effect on interposed tissue must be taken into consideration in this determination. After this the magnets and radiation sources are physically positioned relative to the body (block 158) and treatment is undertaken, according to the scheme (block 160).

The increase in the efficacy of the treatment, for the case of a radiation is given by:

$$\Delta \text{Effectiveness} = \text{Int}^{TT}(\Delta EBS) - (\text{Int}^{IT+PTT}(\Delta EBS)$$

Where Int is the integral over the volume indicated in the superscript and TT=Tumor Tissue; and IT+PTT=Interposed Tissue and Post Tumor Tissue;

And EBS=Effective Beam Strength

The amount of time that the tumor tissue can be irradiated will be limited by the effective strength of the beam as it crosses the tissue that is interposed between the body exterior surface and the effective strength of the beam as it passes through the tissue interposed between the tumor (on the backside relative to the beam source) and the body exterior surface. Accordingly, in a preferred embodiment, the difference between the increase in beam strength between the tumor tissue and the interposed tissue and post tumor tissue is maximized. In one method of doing this a pair of permanent magnets that have been laser aligned are provided and the patient is moved into position between them. With this method the magnets do not have to be moved to be positioned correctly relative to the patient. Such movement could reduce the alignment of the magnets. Also, the magnetic field between the two magnets can be measured while no patient is interposed, to verify alignment and magnetic field strength. Although the presence of a human body will change the field characteristics, it is still helpful to know the magnetic field when no body is interposed. In one preferred embodiment, after the patient is moved into position, while maintaining alignment by the use of a track or guide, the magnets are moved so that they approach or touch the patient's skin on either side. The magnets may be placed slightly toward the anterior of the tumor, referenced to the beam source. In a preferred embodiment, the magnetic field at its maximum point within the tumor, is at the low end of the effective range, so that the magnetic field in the non-tumor areas is below the effective range. Although the magnetic field in these areas may still have some positive effect on the effective beam strength, it is not as great as the effect within the tumor.

In a preferred embodiment, a first radiation beam strength is applied for long enough to raise the concentration of free radicals to a desired level. Then a second radiation beam strength may be applied to maintain the free radical concentration and reactivity at near optimal levels. Sequential fractionation may be employed to maximize the compounding benefits of sequential magnetic field exposures or variable radiation beam strength exposure or exposures designed to optimize for a given free radical composition. That is, the magnetic field strength and/or the radiation beam strength may be varied over time. In at least one user selectable mode the timing and control assembly turns on both the radiation beam assembly to produce a first beam intensity and the magnetic field assembly to produce a first field strength, and after a first time duration reduces beam intensity by at least 20% of the first beam intensity, to a nonzero level, but does not reduce the magnetic field strength by more than 10%, and maintains these levels for a second time duration.

In one preferred embodiment the radiation beam producing device produces a rapidly sequenced magnetic field that, in the tumor, coincides with the exposure to a radiation field of planned strength, variation over time and contour and conforms to a preplanned and contoured electromagnetic field. In one method, the magnetic field continues after the pulse has passed through the tumor, but turns off for a brief period of time, as the beam is passing through interposed tissue. If electromagnets are used, the magnetic field is varied by varying the strength of the electric current through the electromagnets. In the case of permanent magnets (or electromagnets) a rotating shielding can be periodically interposed between the magnets, thereby disrupting the magnetic field.

Figure 8:
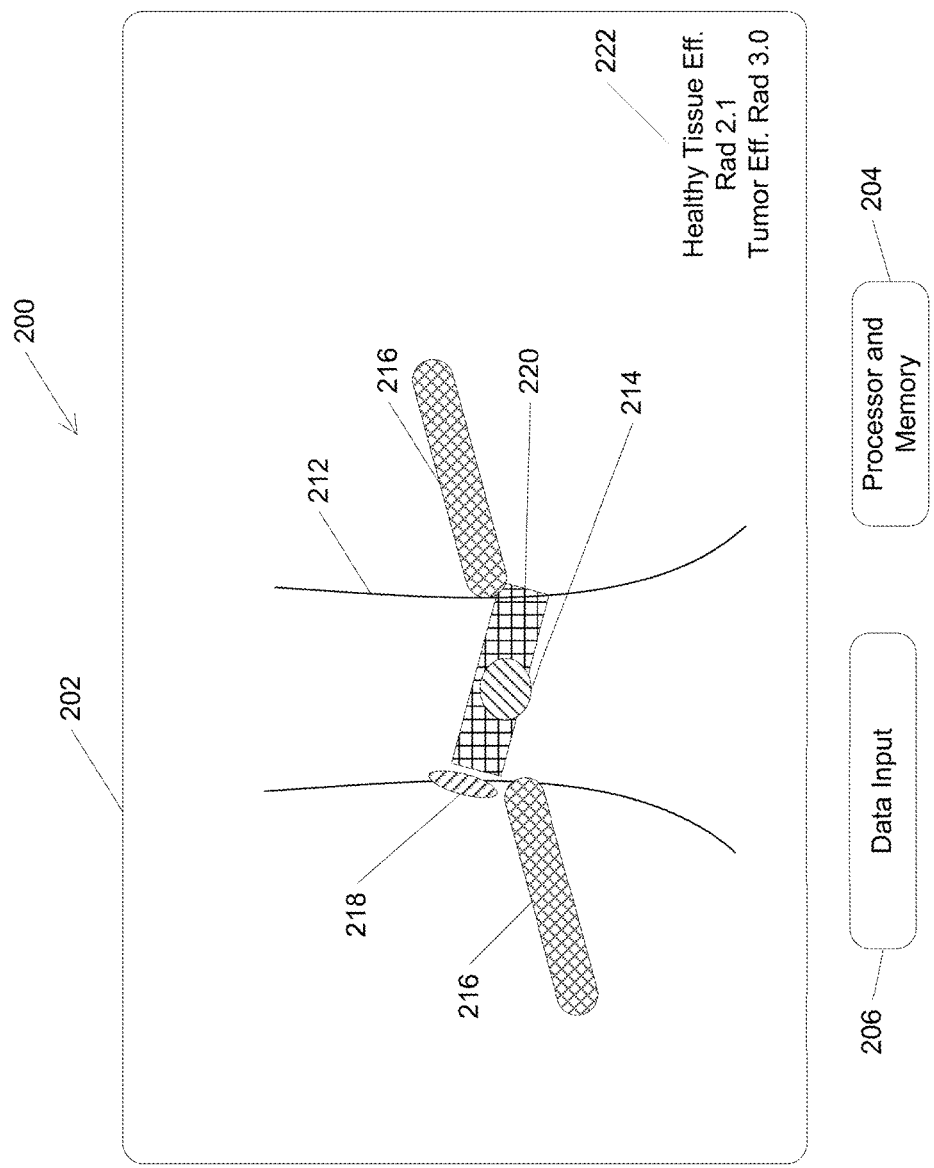
FIG. 8 shows a user station adapted to facilitate the development of a treatment plan.

Referring to FIG. 8, in a preferred embodiment a treatment modeling station 200, having a display screen 202; a standard keyboard and mouse set of input devices 206; and a processor and memory assembly 204, is provided to aid a health care provider in planning treatment. In one embodiment, this device is a standard computer, such as a standard Windows OS, Linux OS or Apple computer, running specialty software. X-ray or ultrasound imagery, in the instance shown showing a patient's abdomen 212 and a tumor 214 in the abdomen 212, may be loaded onto the device memory 204 and displayed, as shown. The health care provider is able to move symbolic shapes indicating magnet 216 and radiation source 218 positions, and increase or decrease magnet and radiation source intensity. A false color map 220 shows the effective beam strength, and a reading of total tumor effective radiation and healthy tissue effective radiation is provided 222, for a given time progression of treatment events, which may be entered and modeled. The time progression can be displayed at either real time or faster than real time, to indicate the effects of treatment. After the radiation source is turned off, a beam may still be shown indicating the continuing effects of free radicals that continue to exist. In one embodiment station 200 is enabled to recommend a treatment sequence.

Figure 9:
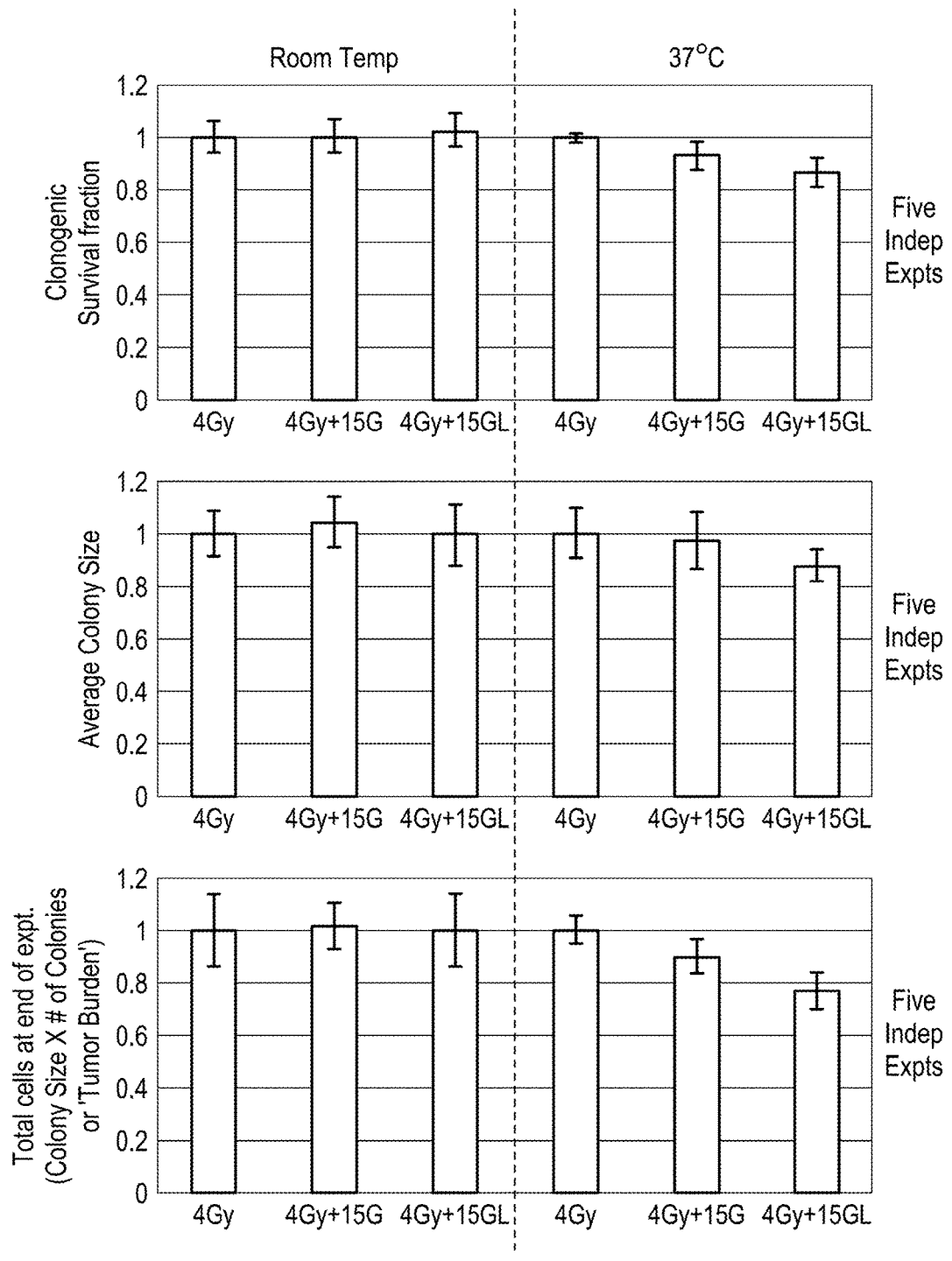
FIG. 9 is a graph showing the effects of tumor radiation and electromagnetic field strength on tumor cell death.

FIG. 9 is a bar graph that shows the effectiveness of 4Gy of gamma radiation in the case where it is not accompanied by a magnetic field, when accompanied by a 15 gauss electromagnetic field (middle column) and when accompanied by a 15 gauss magnetic field that is continued for 15 minutes after the gamma radiation is discontinued.

INDUSTRIAL APPLICABILITY

The present invention finds industrial applicability in the manufacturing of machinery for treating a tumor.

The invention claimed is:

1. A method of creating an elevated concentration of free radicals having augmented lifetimes within a tumor, comprising:
   a. exposing said tumor to a first stimulus sufficient to create an elevated concentration of free radicals in said tumor;
   b. creating a magnetic field that traverses said tumor and that inhibits the recombination of said free radicals in said tumor, thereby augmenting said lifetimes of said free radicals;
   c. ceasing to expose said tumor to said first stimulus;
   d. exposing said tumor to a second stimulus sufficient to sustain an elevated concentration of free radicals in said tumor; and
   e. continuing to create said magnetic field for at least one minute after ceasing said first stimulus, whereby said magnetic field continues to prolong lifetimes of said free radicals.

2. The method of claim 1, wherein said magnetic field has a strength in the range of from 0.5 millitesla to 10 millitesla.

3. The method of claim 2, wherein said magnetic field has a strength in the range of from 1 millitesla to 2 millitesla.

4. The method of claim 1, wherein said magnetic field has a strength in the range of from 0.5 millitesla to 3 millitesla.

5. The method of claim 4, wherein said magnetic field has a strength in the range of from 1.2 millitesla to 1.8 millitesla.

6. The method of claim 1, wherein said first stimulus is electromagnetic radiation having a frequency in the range of $10^{10}$ Hz to $10^{21}$ Hz.

7. The method of claim 1, wherein said first stimulus is electromagnetic radiation having a frequency in the range of $10^{15}$ Hz to $10^{21}$ Hz.

8. The method of claim 1, wherein said magnetic field is of a magnitude that inhibits the interstate crossing of triplet state free radical pairs to singlet state free radical pairs.

9. The method of claim 1, wherein said magnetic field is created by at least one magnet positioned exterior to said tumor.

10. The method of claim 1, wherein said magnetic field is created by magnetic particles that are injected into proximity to said tumor.

11. The method of claim 1, wherein said elevated concentration of free radicals is created by sound waves.

12. The method of claim 1, wherein said elevated concentration of free radicals is created by acoustic cavitation.

13. The method of claim 1, wherein said free radicals interfere with the operation of enzyme within cells of said tumor.

14. The method of claim 1, wherein said magnetic field is contoured, scaled or designed to conform to tumor volume or shape.

15. The method of claim 1, wherein electromagnetic shielding is used about said tumor to block ambient electromagnetic interference from said tumor.

16. The method of claim 1, wherein said creation of said magnetic field continues after said ceasing of said first stimulus, for between 5 minutes and 3 hours.

17. The method of claim 1, wherein said creation of said magnetic field continues after said ceasing of said first stimulus, for between 20 minutes and 2 hours.

18. The method of claim 1, wherein said creation of said magnetic field continues after said ceasing of said first stimulus, for between 40 minutes and 1.5 hours.

19. The method of claim 1, wherein said creation of said magnetic field continues after said ceasing of said first stimulus, for more than 10 minutes.

20. The method of claim 1, wherein said creation of said magnetic field continues after said ceasing of said first stimulus, for more than 30 minutes.

21. The method of claim 1, wherein said creation of said magnetic field continues after said ceasing of said first stimulus, for more than 1 hour.

22. An apparatus for treating a mammal having a tumor, comprising:

a. a radiation beam assembly, producing a first ionizing radiation beam having a first strength that causes free radicals to form in mammalian flesh and a second ionizing radiation beam having a second strength that causes free radicals to be sustained in mammalian flesh;

b. a magnetic field assembly, producing a magnetic field of predetermined strength and dimension, of less than 10 millitesla;

c. a timing and control assembly adapted to coordinate said radiation beam assembly and said magnetic field assembly to produce a time pattern of first ionizing radiation beam production and second ionizing radiation beam production and magnetic field production, said timing and control assembly including a user input device, permitting a user to select said time pattern of first and second ionizing radiation beam production and magnetic field production;

wherein said timing and control assembly includes a set of user selectable modes, said set of user selectable modes including at least one mode wherein said timing and control assembly turns on both said radiation beam assembly to produce said first ionizing radiation beam and said magnetic field assembly, and after a first time duration turns off said first ionizing radiation beam and turns on said second ionizing radiation beam but maintains said magnetic field assembly for a second time duration.

23. The apparatus of claim 22, wherein said radiation beam assembly produces a pulsed discontinuous radiation exposure of planned intensity and said magnetic field assembly is controlled to create a magnetic field having a first intensity in said tumor as each pulse is passing through said tumor and to not create a magnetic field of said first intensity when no pulse is passing through said tumor.

* * * * *